United States Patent [19]
Matsumura

[11] Patent Number: 4,894,778
[45] Date of Patent: Jan. 16, 1990

[54] X-RAY COMPUTERIZED TOMOGRAPHIC DEVICE

[75] Inventor: Shigeru Matsumura, Tokyo, Japan

[73] Assignee: Yokogawa Medical Systems, Limited, Tokyo, Japan

[21] Appl. No.: 245,356

[22] Filed: Sep. 16, 1988

[51] Int. Cl.$^4$ .......................... G06F 15/42; G01T 1/17
[52] U.S. Cl. .................................. 364/413.15; 378/901
[58] Field of Search ....................... 364/413.13, 413.14, 364/413.15, 413.16, 413.19; 378/4, 9, 10, 19, 901

[56] References Cited

U.S. PATENT DOCUMENTS

| | | |
|---|---|---|
| 4,411,011 | 10/1983 | Le May ................................. 378/4 |
| 4,637,040 | 1/1987 | Sohval et al. ........................ 378/19 |
| 4,677,554 | 6/1987 | Dobbs et al. .......................... 328/19 |
| 4,686,692 | 8/1982 | DeMeester et al. ................ 378/901 |
| 4,754,468 | 6/1988 | Mori ...................................... 378/4 |

Primary Examiner—Jerry Smith
Assistant Examiner—Kim Thanh Tbui
Attorney, Agent, or Firm—Moonray Kojima

[57] ABSTRACT

An X-ray computerized tomographic device of this invention provides images of good quality based on view-interlacing without complicating gantry rotation and scan data sampling control, and which is characterized by setting $N \cdot M - 1$ units of sampling points (M and N being positive intergers) around a subject over which a rotary scan is performed continuously M times by skipping the $M - 1$ sampling point.

2 Claims, 6 Drawing Sheets

X-RAY COMPUTERIZED TOMOGRAPHIC DEVICE

FIELD OF THE INVENTION

This invention relates to an X-ray computerized tomographic device that collects radiation projection data from multiple directions along the sections of a subject, and reconfigures tomographic images based on such collected data. More specifically, this invention provides an improved means to collect radiation projection data.

DESCRIPTION OF THE PRIOR ART

It has been commonly known that an X-ray computerized tomographic device (or simply a CT device) reconfigures the tomographic image of a subject by radiating an X-ray beam onto a subject from multiple angles along the sections of the subject to collect projection data (or scan data) for subsequent scan data processing on a computer.

FIG. 7 is a block diagram showing the major parts of such a CT device. In FIG. 7, "1" indicates an X-ray tube installed opposite to detector 2 with tomographic area 3 located in between. These parts are installed on a gantry (not illustrated) that maintains the above positional relationships. X-ray tube 1 and detector 2 rotate around subject 4 placed in tomographic area 3 under the control of a gantry controller (not shown in the diagram). Detector 2 is equipped with several hundred detection device channels arranged in a circular arc to detect X-ray 5 in a fan beam form radiated from x-ray tube 1 passing through tomographic area 3. Data collection unit 6 is provided with the means to integrate signals detected by detector 2 for a specific duration of time, and collects these signals at a specific timing, amplifies the collected signals, and converts the output signals into digital data for transfer to the next stage. Computer 7 is equipped with a means for storing the data transferred from data collection unit 6, and operates the image reconfiguration by using the stored data, displays images on CRT 8 according to the operation results, and sends specific signals to individual sections of the CT device according to signals received from keyboard 9. In the above configuration, the CT device rotates X-ray tube 1 and the detector 2 in a specific direction (clockwise for example), radiates X-ray beams to subject 4 at multiple predetermined angular positions (view positions or sampling points), then collects the scan data. When collecting the scan data, this device completes gantry acceleration and sets a constant speed rotation before reaching reference anglular position $P_0$ after moving over the approach section. The CT device starts collecting scan data when X-ray tube 1 passes over reference angular position $P_0$ and continues scanning until it reaches the overlapped section when the first rotation of scan data collection is completed. The angle of gantry rotation in this scan is an aggregate of the angle corresponding to the approach section, the angle corresponding to the deceleration section travel until the rotation stops, and the angle corresponding to overlapped section plus 360°. For the next scan, the section (slice surface) of the subject is changed and the gantry is rotated counterclockwise at the same angles as the previous scan so that scan data can be collected from each sampling point. Then, the above operation is repeated to collect scan data on the desired slice surfaces. The general method of collecting scan data is described above. To improve the quality of reconfigured images, the following scan methods may be used:

One method, as shown in FIG. 8., uses clockwise and counterclockwise scans to collect scan data for two rotations; the images reconfigured according to respective scan data are added and averaged for display. This enables an S/N ratio equivalent to twice the X-ray dosage to be obtained. The other method is used to collect scan data by interlacing views between clockwise and counterclockwise rotations to reconfigure images based on the data collected. In this case, the view-interlacing collects, data at sampling points $X_1$, $X_3, \ldots, X_{15}$ during a clockwise rotation, and at $X_{16}$, $X_{14}, \ldots, X_2$ during a counterclockwise rotation as shown in FIG. 8. When using such view-interlacing, the creation of artifacts due to insufficient views can be reduced while improving the image quality. However, these scan methods use scan intervals between the clockwise and counterclockwise rotations that accompanies the directional switching of gantry rotation. This may reduce the resolution of reconfigured images, and more artifacts may be created due to the movement of the subject body. Moreover, for scanning using view-interlacing, gantry rotation or sampling points control may become complicated.

SUMMARY OF THE INVENTION

This invention is intended to overcome the disadvantages of the prior art by providing an X-ray computerized tomographic device that can provide images of good quality without complicating gantry rotation and scan data sampling control. Another object of this invention is to provide an X-ray computerized tomographic device that enable multiple methods of scanning without complicating a gantry rotation and scan data sampling control. The X-ray computerized tomographic device based on this invention is characterized by:

Setting sampling points of $N \cdot M - 1$ (N and M being positive integers) around a subject;

Scanning the sampling points around by skipping $M - 1$ point and continuously repeating such scanning for M times; and Collecting the scan data at every sampling point.

DETAILED DESCRIPTION OF THE INVENTION

Figure 1:
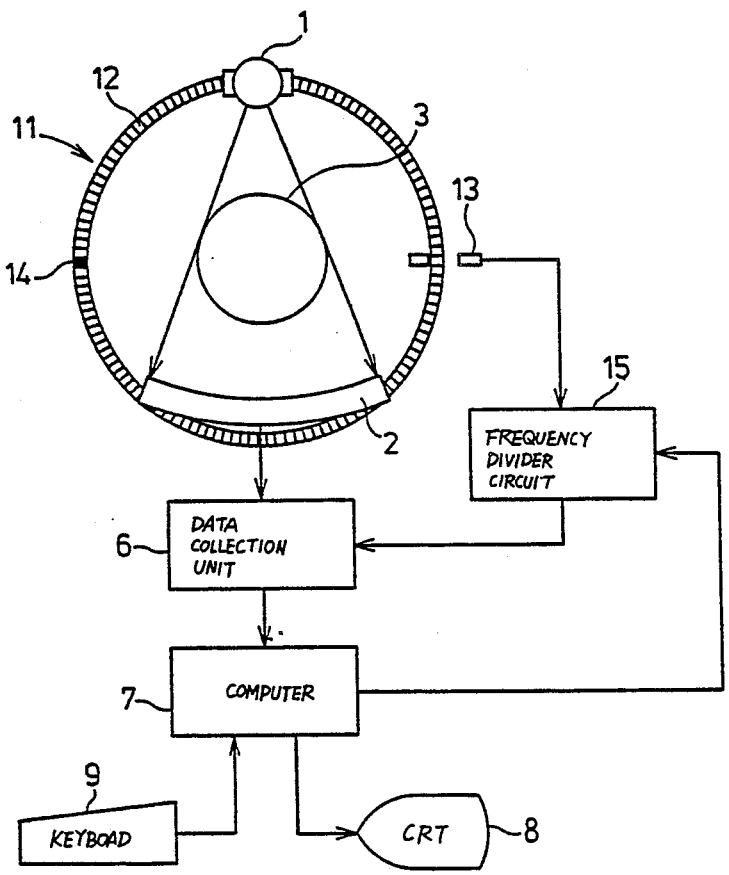
FIG. 1 shows a block diagram of a CT device of a typical application mode the this invention.

The preferred application modes of this invention are described in detail by using examples by referring to the accompanying drawings as follows:

FIG. 1 shows a conceptual block diagram of the major parts of a CT device that reflects a preferred application mode of this invention.

In FIG. 1, X-ray tube 1, which irradiates a continuous X-ray beam, is installed opposite detector 2 on the gantry frame (not shown in the figure) with tomographic area 3 located in between. On the gantry, marker device 12 of $N \cdot M - 1$ units of rotary encoder 11 is installed. The gantry is controlled by the gantry controller (not shown in the figure) to rotate continuously around tomographic area 3 in a specific direction for a minimum of M times. The rotary position of the gantry at this time is detected by fixed marker detector 13 of rotary encoder 11. Rotary encoder 11 may have a configuration in which marker device group 12 is fixed, while marker detector 13 rotates with the gantry. Among marker device group 12, absolute position marker device 14 is installed to detect the rotation reference position of X-ray tube 1 and detector 2. An output signal from marker detector 13 is sent to frequency divider circuit 15, which divides it at a rate of 1/M and sends it to data collection unit 6 as a scan data sampling instruction signal. Data collection unit 6 collects scan data from detector 2 in synchronization with the sampling instruction signal and transfers the signal to computer 7 after the specified processing is executed. Computer 7 reconfigures an image based on the data. Computer 7 provides the frequency divider circuit 15 with the dividing ratio set from keyboard 9.

Figure 2:
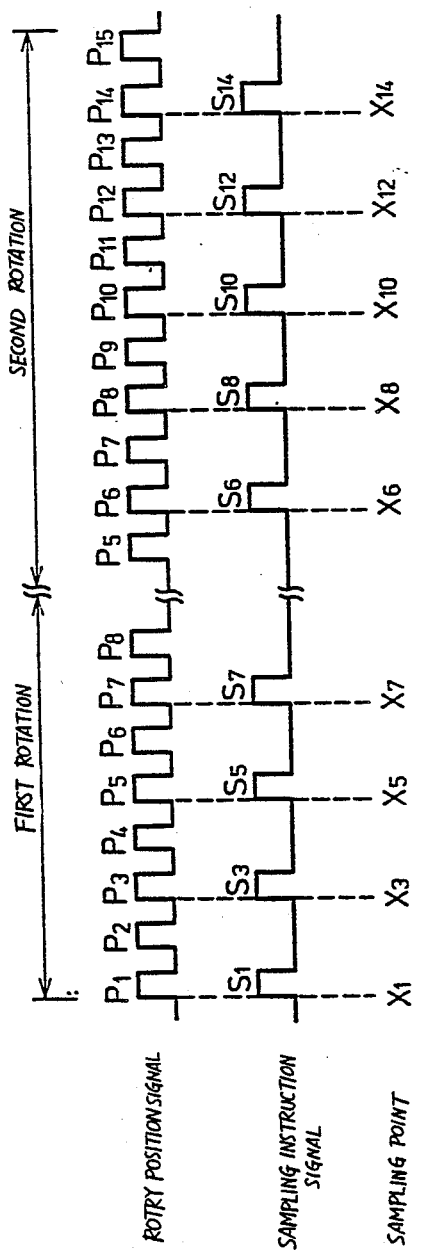
FIG. 2 shows the relationship between a rotary position signal of the gantry and scan data sampling.

The scan data collection operation of a CT device having the above configuration is described as follows: For the sake of descriptive convenience, let $N = 8$, $M = 2$. Therefore, the number of the rotary encoder marker device is 15 and the dividing ratio of frequency divider circuit 15 is ½. In an actual device, a value of several hundreds is set for N and M is an integer significantly smaller than N. In this following description, the marker devices are called $M_1, M_2, \ldots, M_{15}$. Moreover, absolute position marker device 14 is called marker device $M_1$. The gantry is controlled by the gantry controller as it rotates clockwise, for example, at least two times. During these two rotations, marker detector 13 outputs rotary position signals $P_1, P_2, \ldots, P_{15}$ twice via marker devices $M_1, M_2, \ldots, M_{15}$ as shown in FIG. 2. Frequency divider circuit 15 outputs the sampling instruction signal after dividing the rotary position signals into ½.

Figure 3:
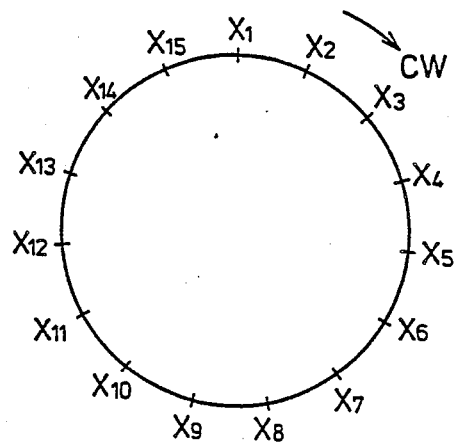
FIG. 3 shows a schematic diagram of the sampling point arrangement in a preferred application mode of this invention.

Accordingly, at the end of the first gantry rotation, sampling instruction signals $S_1, S_3, S_5, S_7, \ldots, S_{15}$ are output to match rotary position signals $P_1, P_3, P_5, P_7, P_{15}$. At the end of the second rotation, sampling instruction signals $S_2, S_4, S_6, S_8, \ldots, S_{14}$ are output to match rotary position signals $P_2, P_4, P_6, P_8, \ldots, P_{14}$. According to these sampling instruction signals, data collection unit 6 collects scan data at respective rotary positions of the gantry. If a gantry rotary position is expressed by the rotary position of X-ray tube 1 when X-ray tube 1 sequentially reaches positions $X_1, X_3, \ldots, X_{15}, X_2, X_4, \ldots, X_{14}$ on the rotary orbit as shown in FIG. 3, scan data is collected individually. These positions on the rotary orbit where data is collected at are called sampling points. Accordingly, data collection based on sampling instruction signals is done by tracing the fifteen sampling points $(X_1, X_2, \ldots, X_{15})$ by skipping one point alternately until the data from all sampling points are collected after two rotations. The data collected by two gantry rotations is done through view-interlacing, which can be achieved by simply rotating the gantry two times in succession. In this way, there are no scan intervals between the first and second rotation like the application modes based on prior art as previously described. Moreover, gantry rotation and the scan data sampling mode need not be changed. In other words, scan data can be collected through view-interlacing under simple control. The image reconfiguration based on such scan data provides images of high resolution with minimized artifacts.

Figure 4:
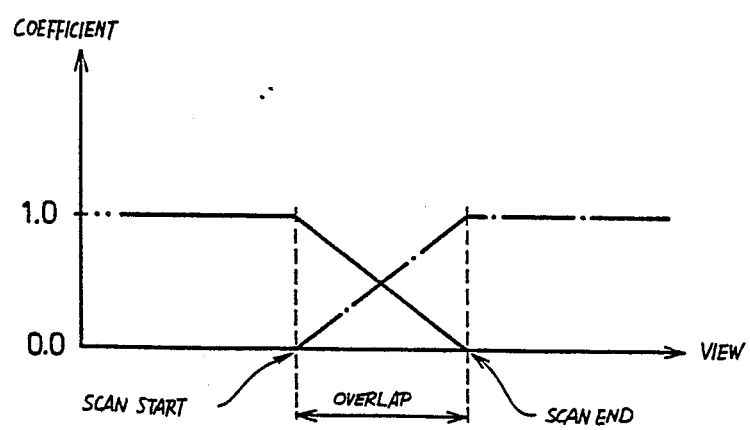
FIG. 4 explains an overlapped scan.

If scan data is collected by rotating the gantry multiple times, the scan data collected during the preceding rotation and following rotation will be mutually set according to the view-interlacing relationship. Therefore, each combination of scan data obtained through these rotations in the preceding/following relationships will be scan data collected through view-interlacing. Therefore, if scan data is collected by rotating the gantry multiple times without changing the slice surface of a subject, view-interlaced scan data for the cine-mode can be obtained. If no view-interlaced scan data is needed for the cine-mode, the scan data respectively obtained from each rotation can be the cine-mode data. In this case, a cine-mode image with high time resolution can be obtained. In this case, however, the sampling points for the first rotation will be $X_1, X_3, \ldots, X_{15}$, or $X_1, X_3, X_{15}, X_2$ and the interval between sampling points $X_1$ and $X_{15}$ or $X_1$ and $X_2$ will be one half that of the other intervals. If such data is used for image reconfiguration as is, artifacts will be created due to an irregular distribution of sampling intervals or views. To prevent this, an overscan method applied to correct body movement is very effective. According to this method, scan data is collected from scanning that slightly exceeds one full rotation so that the data from an overlapped section will be synthesized by padding it for addition as shown in FIG. 4. This process reduces the artifacts created by irregular view distribution.

Figure 5:
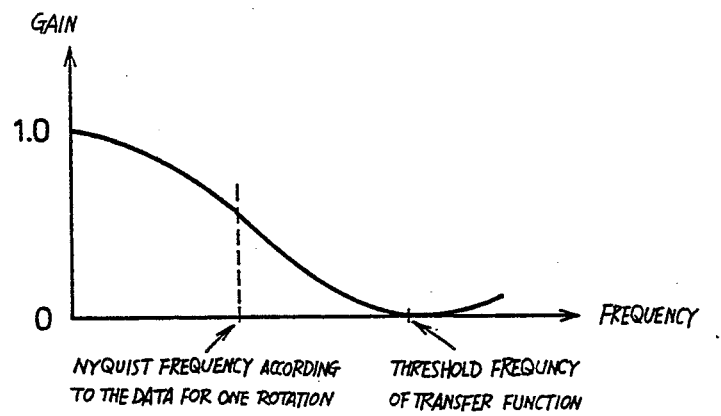
FIGS. 5 and 6 show the transfer function of dislocation in the direction of rotation in a continuous X-ray CT device.
Figure 6:
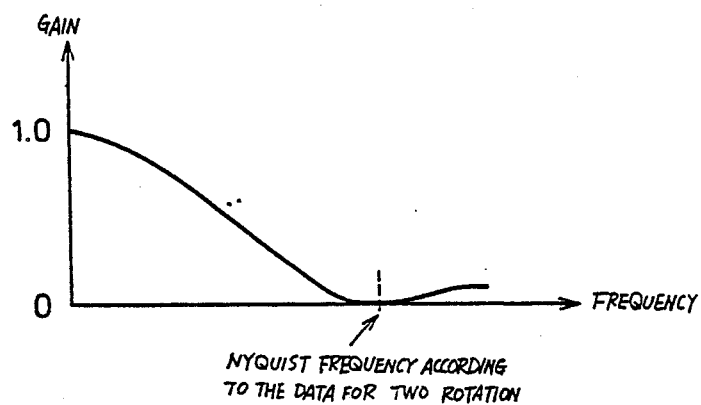
Figure 7:
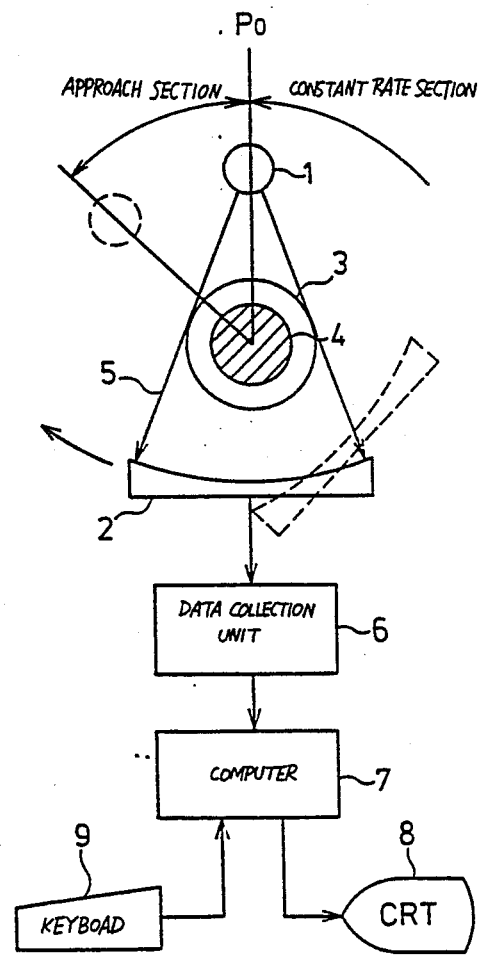
FIG. 7 shows a block diagram of an approximate configuration of a CT device based on prior art.
Figure 8:
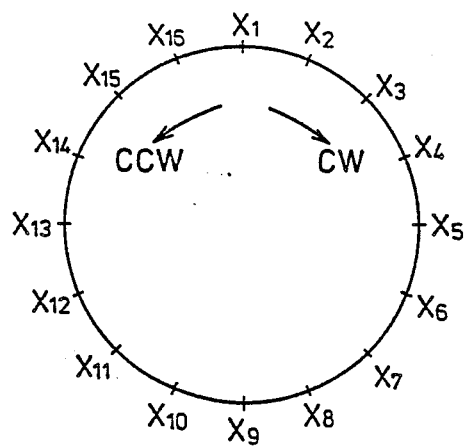
FIG. 8 is a schematic diagram showing the scan data sampling of a CT device based on prior art.

For continuous X-ray radiation, the gantry continues rotary movement while data collection unit 6 integrates the data from the detector. Consequently, resolution in the direction of rotation is deteriorated. For a single rotation scan, the Nyquist frequency in the transfer function of dislocation becomes ½ that of the threshold frequency of the transfer function as shown in FIG. 5. However, if two rotations for a view-interlacing scan are done, an overlapped scan occurs between mutually adjacent sampling points on the rotary orbit of the gantry. This causes the Nyquist frequency to be doubled to match the threshold frequency of the transfer function as shown in FIG. 6. Therefore, deteriorated resolution in the direction of rotation can be recovered up to the vicinity of the threshold frequency.

Moreover, the above mentioned scan data collection method has been described with specific values given to the numbers of rotary encoder marker devices and dividing ratio of the frequency divider circuit for descriptive convenience. This invention, however, is not restrictive regarding such specified values. Moreover, in the above mentioned application mode in which an X-ray tube and detector rotate as a single body, the detection device group may be arranged by fixing them along the circumference, and the X-ray tube can be structured to rotate continuously.

We have described the preferred application mode of this invention. This invention may easily applied in other specific forms by persons possessing the technical knowledge in fields to which this invention is applicable without departing from the spirit or essential characteristics of the following claims.

I claim:

1. An X-ray computerized tomographic device comprising
    a radiation source (1) rotatable in a rotary orbit around a subject to be examined while continuously radiating X-ray beams along sections of said subject;
    a radiation detector (2) disposed opposite said radiation source with said subject being disposed therebetween, said radiation detector comprising a plurality of detection devices for detecting radiation in said subject, said radiation detector generating sample output signals when the position of said radiation source matches one of a plurality of sampling points arranged at equal intervals on said rotary orbit of said radiation source;
    data collection means (6, 11, 15) for collecting data from said radiation detector at N·M−1 sampling points, wherein N is an integer, during M rotations of said rotation source in the same direction, wherein data is collected from a forward sampling point after skipping an M−1 sampling point adjacent to a point from which data was collected during a specific rotation, said data collecting means comprises a rotary encoder comprising N·M−1 marker means, and means for frequency dividing an output signal from said rotary encoder at a rate of 1/M and for outputting a sample time signal to said marker means; and
    a computer (7) for reconfiguring collected data into tomographic images of said subject.

2. The device of claim 1, wherein said computer comprises means for reconfiguring sectional images of said subject based on data collected during M rotations of said radiation source with interleaving of data from the respective rotations.

* * * * *